US012811015B2

(12) United States Patent
Somani et al.

(10) Patent No.: US 12,811,015 B2
(45) Date of Patent: Nov. 24, 2026

(54) SYSTEM AND METHOD FOR PULMONARY EMBOLISM DETECTION FROM THE ELECTROCARDIOGRAM USING DEEP LEARNING

(71) Applicant: Icahn School of Medicine at Mount Sinai, New York, NY (US)

(72) Inventors: Sulaiman Somani, New York, NY (US); Benjamin Glicksberg, New York, NY (US); Girish Nadkarni, New York, NY (US)

(73) Assignee: Icahn School of Medicine at Mount SInai, New York, NY (US)

( * ) Notice: Subject to any disclaimer, the term of this patent is extended or adjusted under 35 U.S.C. 154(b) by 0 days.

(21) Appl. No.: 19/327,897

(22) Filed: Sep. 12, 2025

(65) Prior Publication Data

US 2026/0058021 A1 Feb. 26, 2026

Related U.S. Application Data

(62) Division of application No. 17/746,463, filed on May 17, 2022, now Pat. No. 12,424,327.

(51) Int. Cl.
*G16H 50/30* (2018.01)
*G16H 50/20* (2018.01)

(52) U.S. Cl.
CPC ............. *G16H 50/30* (2018.01); *G16H 50/20* (2018.01)

(58) Field of Classification Search
None
See application file for complete search history.

(56) References Cited

U.S. PATENT DOCUMENTS

2010/0125173 A1* 5/2010 Bottai .................... G16H 50/50 600/300
2012/0190992 A1* 7/2012 Liao ..................... A61B 5/0215 600/485
2017/0004619 A1* 1/2017 Liang .................. G06V 10/454

OTHER PUBLICATIONS

Huang, SC., Pareek, A., Zamanian, R. et al. Multimodal fusion with deep neural networks for leveraging CT imaging and electronic health record: a case-study in pulmonary embolism detection. Sci Rep 10, 22147 (2020) (Year: 2020).*

(Continued)

*Primary Examiner* — Joseph D Burgess
(74) *Attorney, Agent, or Firm* — Leason Ellis LLP

(57) ABSTRACT

A method of assessing a likelihood of a patient having a pulmonary embolism (PE) comprises receiving discrete patient data, including patient-related clinical and demographic data pertinent to the patient, receiving electrocardiograph (ECG) waveform data obtained from examination of the patient, processing both the received discrete patient data and received set of ECG waveform data using a supervised deep learning multimodal fusion model that has been trained using analogous input training data including both discrete patient data and ECG waveform data to obtain an optimal match to results from corresponding patient computed tomography pulmonary angiograms (CTPA), indicative of a presence or absence of a pulmonary embolism, and outputting a measure of the likelihood of the patient having a pulmonary embolism.

18 Claims, 10 Drawing Sheets

(56) References Cited

OTHER PUBLICATIONS

Sharma LN, Dandapat S, Mahanta A. Multichannel ECG data compression based on multiscale principal component analysis. IEEE Trans Inf Technol Biomed. Jul. 2012;16(4):730-6. doi: 10.1109/TITB.2012.2195322. Epub Apr. 19, 2012. PMID: 22542694. (Year: 2012).*

Islam Nu, Gehlot S, Zhou Z, Gotway MB, Liang J. Seeking an Optimal Approach for Computer-Aided Pulmonary Embolism Detection. Mach Learn Med Imaging. Sep. 2021;12966:692-702. doi: 10.1007/978-3-030-87589-3_71. Epub Sep. 21, 2021. PMID: 35695860; PMCID: PMC9184235. (Year: 2021).*

Rucco M, Sousa-Rodrigues D, Merelli E, Johnson JH, Falsetti L, Nitti C, Salvi A. Neural hypernetwork approach for pulmonary embolism diagnosis. BMC Res Notes. Oct. 29, 2015;8:617. doi: 10.1186/s13104-015-1554-5. PMID: 26515513; PMCID: PMC4627406 (Year: 2015).*

* cited by examiner

SYSTEM AND METHOD FOR PULMONARY EMBOLISM DETECTION FROM THE ELECTROCARDIOGRAM USING DEEP LEARNING

CROSS-REFERENCE TO RELATED PATENT APPLICATIONS

This application is a divisional of U.S. patent application Ser. No. 17/746,463, filed May 17, 2022, the entire contents of which is incorporated by reference herein as if expressly set forth in its respective entirety herein.

FIELD OF THE DISCLOSURE

The present disclosure relates to systems and methods for medical diagnosis, and more particularly relates to a system and method for pulmonary embolism detection from electrocardiogram (ECG) data using deep learning.

BACKGROUND OF THE DISCLOSURE

Pulmonary embolism (PE) is a life-threatening complication of venous thromboembolism with high short and long-term cardiovascular morbidity and mortality globally. Given the lack of specificity in presenting symptoms and existing clinical decision rules, diagnostic uncertainty in PE remains high and requires clinicians to use thoracic imaging modalities, most commonly computed tomography pulmonary angiography (CTPA), to confirm diagnosis, especially in those who are at moderate to high suspicion of PE. Over-reliance on CTPA has important implications for resource utilization. For example, in a multi-center analysis of medical centers in the United States, only 3.1% of CTPA scans were positive for PE. More importantly, widespread CTPA confers risk to patients through large radiation doses and may be contraindicated in specific subpopulations.

An effectively developed framework improving CTPA diagnostic yield for PE using routinely collected clinical information would have crucial implications for PE detection and management, increasing patient safety, and mitigating systemic inefficiencies.

SUMMARY OF THE DISCLOSURE

In one aspect, the present disclosure provides a method of assessing a likelihood of a patient having a pulmonary embolism (PE). The method comprises receiving discrete patient data, including patient-related clinical and demographic data pertinent to the patient, receiving electrocardiograph (ECG) waveform data obtained from examination of the patient, processing both the received discrete patient data and received set of ECG waveform data using a supervised deep learning multimodal fusion model that has been trained using analogous input training data including both discrete patient data and ECG waveform data to obtain an optimal match to results from corresponding patient computed tomography pulmonary angiograms (CTPA) indicative of a presence or absence of a pulmonary embolism, and outputting a measure of the likelihood of the patient having a pulmonary embolism.

In another aspect, the present disclosure provides a method of training a computer system to predict whether a patient has a pulmonary embolism (PE) based on discrete patient data, including patient-related clinical and demographic data, and ECG waveform data. The method comprises gathering training data pertaining to a patient population comprising, for each member of the patient population, a computer tomography pulmonary angiogram (CTPA) test, discrete patient data including patient related clinical and demographic data, and ECG waveform data, annotating, for each member of the population, the training data according to a corresponding result of the CTPA, and training a supervised deep learning multimodal fusion model that takes as input the annotated training data and determines weightings of various features of the training data that optimize an accuracy of a match to the CTPA results.

These and other aspects, features, and advantages can be appreciated from the following description of certain embodiments of the invention and the accompanying drawing figures and claims.

DEFINITIONS

Figure 1:
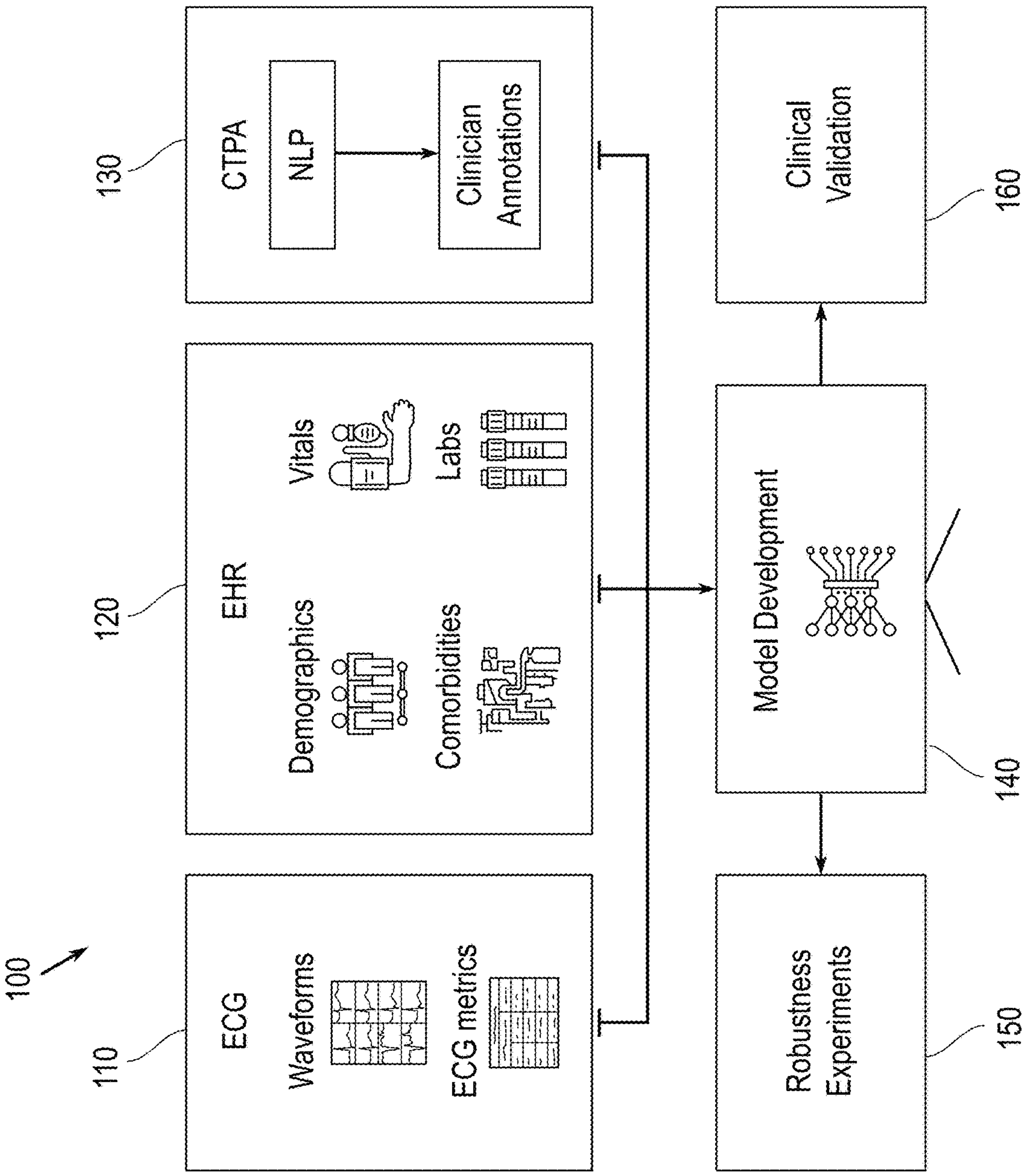
FIG. 1 is a high-level schematic diagram illustrating an embodiment of a general schema for development of a PE detection deep learning model from selected data inputs according to the present disclosure.

Discrete patient data: for the purposes of this application "discrete patient data" should be understood to mean any discrete data that can be considered as potentially significant to the pulmonary health of a patient to those of ordinary skill in the art. Thus, discrete patient data is intended to include patient-related clinical and demographic data including, but not limited to: age, sex, presence of comorbidities including but not limited to arrhythmia, coronary artery disease, cancer, chronic kidney disease, coagulopathy, chronic obstructive pulmonary disease, diabetes mellitus, a history of or pulmonary embolism or deep vein thrombosis (DVT), congestive heart failure, and hypertension, rheumatological disease, pulmonary hypertension, and other health status and clinical criteria including but not limited to pregnancy status, heart rate, systolic blood pressure, diastolic blood pressure, respiration rate, oxygen saturation, brain natriuretic peptide (BNP) level, D-dimer level, troponin level, PR interval length, QRS duration, and QTc length. It is noted that the different data of which the discrete patient data is comprised can be continuous in nature (e.g., troponin level, QRS duration). The data is considered to be discrete in the sense that the values can be assembled easily in a tabular form.

Deep Learning: a type of machine learning based on artificial neural networks in which multiple layers of processing are used to extract progressively higher-level features from data. One or more of a deep learning network the layers may be "hidden" in that they do not directly process data inputs or outputs and their values of their nodes are thus not directly observable.

Semi-supervised machine learning model: a subtype of a supervised machine learning model that uses datasets that are only partially annotated or labeled.

Self-supervised machine learning model: a subtype of supervised machine learning in which datasets are not explicitly labeled or annotated but instead include other types of data (e.g., metadata, correlations) which can be used, at least in part, in a supervisory manner.

DESCRIPTION OF CERTAIN EMBODIMENTS OF THE DISCLOSURE

The present disclosure describes a fusion modeling framework that integrates ECG waveform data and discrete patient data, including patient clinical data, to predict the likelihood of acute PE. The modeling framework utilizes a deep learning-based framework that embeds representations of ECG waveforms and combines these representations synergistically with clinical data, and then generates a classifier model to detect PE in those patients with at least moderate PE suspicion. It is found that the integration of different data modalities and analytic approaches aids in improving prediction. Deep learning models leverage non-traditional data forms (such as raw ECG waveforms) in contrast to other classes of models due to their ability to computationally derive features without pre-specification. In particular, deep learning approaches provide the ability to detect subtle signals indiscernible to clinicians and effectively augment the clinical workflow. The training and execution of the machine learning methods described herein can be conducted in connection with a cloud-based platform.

FIG. 1 is a high-level schematic diagram illustrating an embodiment of a general schema 100 for development of a PE detection model from selected data inputs according to the present disclosure. As shown, the data inputs are selected from two categories: ECG data 110; electronic health record (EHR) data 120. The outputs of the model (for supervised models) consist of computed tomography pulmonary angiography (CTPA) data 130. The ECG data 110 can include raw ECG waveform data, which records electrical activity of the heart as measured by electrodes placed on the patient, as well as specific morphology parameters in tabular form (e.g., PR-interval length, ventricular rate) and physician-confirmed diagnostic reads. The EHR data 120 can include a number of different medical diagnostic factors, including but not limited to, patient demographics, comorbidity information, vital statistics, and laboratory results. It is noted that EHR data can include any and all of the data encompassed by the term "discrete patient data" defined above. For the sake of brevity, the abbreviation "EHR data" is used throughout this section. The CTPA data 130 consists of results of patient CT scans. At a broad level, the CTPA data is annotated as either negative, indicating absence of PE, or positive, indicative of presence of PE. The positive PE data can be further annotated with additional information including the severity, chronicity, and vascular location of the PE. This additional data is added by medical practitioners based on their interpretation of the CT scan images.

All of these distinct categories of data 110, 120, 130 are used to inform model development 140, which is therefore termed "a multimodal fusion model" from the fusion of the distinct categories of data. Model development 140 comprises the design and training of a machine learning model that assigns weights to the various features of the input data so as to generate an optimal match between the input data and the annotated output data. In doing so, the machine learning model "learns" which input factors (i.e., ECG and EHR features) are most significant in determining the likelihood of whether a patient is PE positive or negative and in assessing the likelihood of characteristics of the PE, including severity, chronicity, and location.

During model development, a number of different machine learning approaches can be utilized and combined. It has been found that deep learning models can leverage non-traditional data forms (such as raw ECG waveforms) and set themselves apart from other classes of models by their ability to computationally derive features without pre-specification. In particular, convolutional neural networks (CNNs) have proven to be especially useful in parsing graphical data. CNNs are a class of neural networks having multiple processing layers in which image analysis filters, known as convolutions, are applied. By convolving multiple filters across the image, different features of the image can be highlighted to promote recognition of the image contents. Initial layers of a given CNN can highlight simply features such as edges, border and simple shapes, while deeper layers can be used to identify more complex structures. As the ECG waveform data can be formatted in graphical (image) form, CNNs can be usefully applied to analysis of the graphical data. However, other types of deep learning algorithms can also be employed in model development 140 including, but not limited to recurrent neural networks (RNNs), long-short-term memory networks (LSTMs), graph neural networks, and transformer networks.

Model development 140 can also include techniques for reducing the dimensionality of large data sets having numerous features. This can be done both to improve analysis speed and to improve model performance. It is particularly useful to reduce the dimensionality of the ECG waveform data. Principal component analysis (PCA) is a technique which projects data that contains a large number of features onto a space that contains a smaller number of features that are determined to be most significant. It is noted that in PCA, the features of the reduced-dimension set do not necessarily correspond to any of the individual features in the data set and can be therefore thought of as combined features. This feature of PCA can reveal connections that would otherwise be hard to discern by conventional medical interpretation.

Other dimensionality reduction techniques that can be used in the context of the present disclosure include, but are not limited to, other linear techniques such as Factor Analysis (FA), Linear Discriminant Analysis (LDA) and Truncated Singular Value Decomposition (SVD), non-linear techniques such as Kernel PCA, t-distributed Stochastic Neighbor Embedding (t-SNE), Multidimensional Scaling (MDS), and Isometric mapping (Isomap), and feature elimination techniques such as random forests.

Another important aspect of the model development 140 pertains to the sufficiency of the annotated data. Ideally, each patient in the data set used for training is associated with ECG data taken from the patient, EHR data recorded by a medical practitioner near to the time that the ECG was taken, and an annotated CTPA data associated with a CT scan obtained near to the time of the ECG. In other words, each patient ideally has a full set of input data and output data from which a machine learning algorithm can be trained. However, in a large data set, some annotated CTPA data can be missing or questionable due to timing or other concerns. This can be an important issue because the accuracy of a supervised machine learning algorithm is maximized by full annotation of the output data. To deal with the issue, semi-supervised and/or self-supervised algorithms can be used which modify a "full" supervised algorithm to account for partially annotated or non-annotated output (CTPA) data.

Additionally, in certain implementations, "synthetic" data can be used to enhance the data set with the aim of increasing the robustness of the training algorithm. One way to do this is to generate synthetic ECG waveforms from original patient data by invoking algorithms such as generalized adversarial networks (GANs) that are adapted for this operation. In a GAN, a generator engine creates new data examples from sample real input data by adding random variation. A discriminator engine is trained, using both real data and the generated synthetic data, to be able to distinguish between the real and synthetic data. The engines effectively compete, with the discriminator engine learning to get better at distinguishing the generated fake data and real data and the generator engine learning to generate more realistic data points. This process continues until the synthetic data generator engine can create synthetic data instances that the discriminator cannot distinguish from real data. In this way additional data can be introduced if needed in the overall training process for PE detection and classification.

Referring again to FIG. 1, once a machine learning model has been developed and trained, it is subject to robust testing 150 and clinical validation 160. The testing of the model involves testing various performance metrics of the model on sets of ECG/EHR inputs that are distinct from the data used to train the model. Testing can involve numerous iterations and testing different variables in the models such as learning rates, regularization, and other hyperparameters. Clinical validation involves comparing new predictions of PE generated by the model against clinical assessments of PE of the same input data. Embodiments of the model discussed further below were robustly tested and validated in this manner.

Model Development Example

Figure 7:
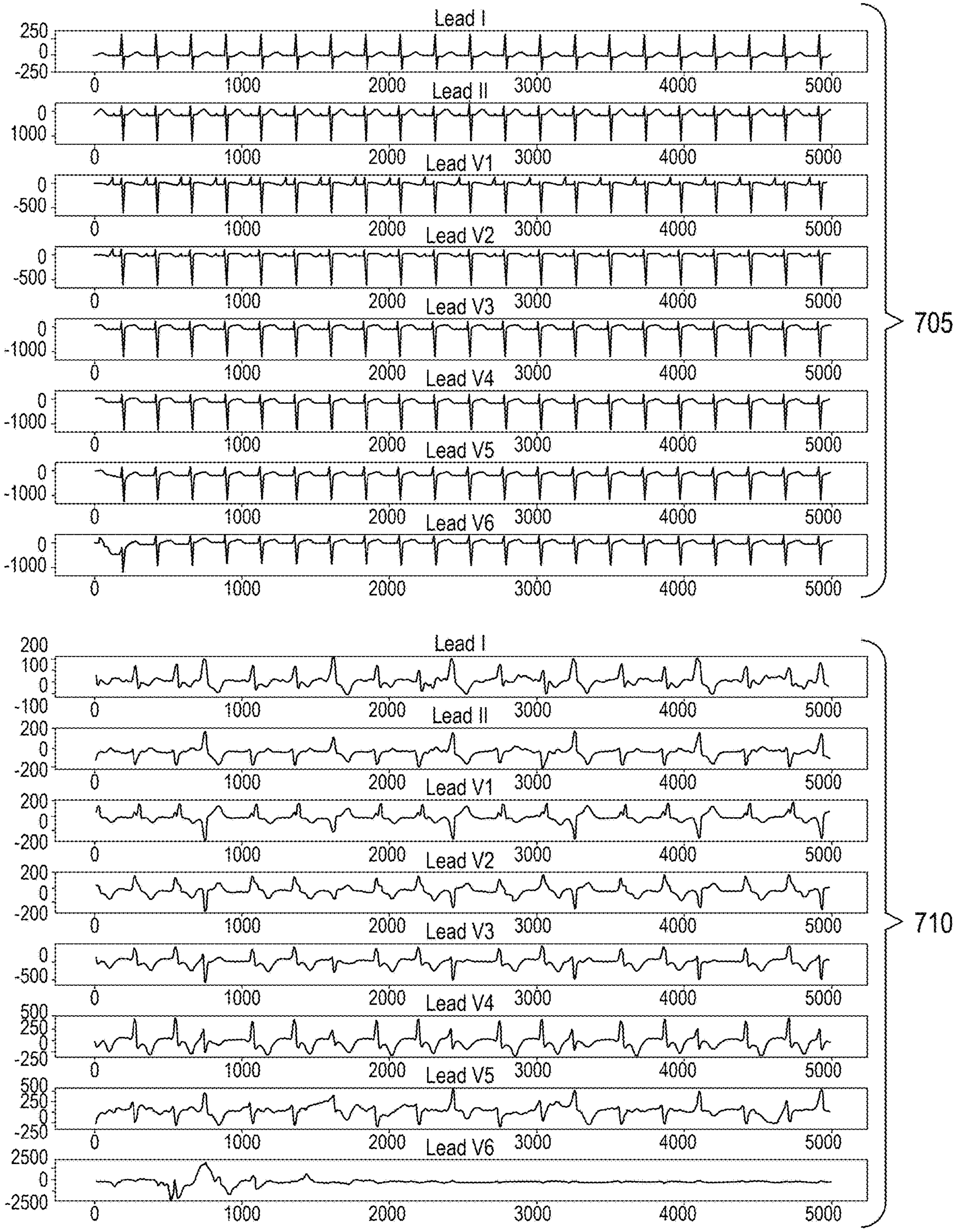
FIG. 7 shows exemplary ECG waveform data (of both good and poor quality) obtained for training a deep learning framework for detection PE according to an embodiment of the disclosure.

In one implementation of deep learning model development for prediction of PE according to the present disclosure, data was obtained from patients at moderate-to-high suspicion of PE using data between Jan. 1, 2003 to Jun. 3, 2020 from five hospitals in the Mount Sinai Health System (New York City, New York) serving a diverse, urban population. In one study, a total of 30,109 potential CTPAs were retrieved. After Natural Language Processing (NLP)-augmented annotation of these reports, a total of 28,496 CTPA reports were labeled, of which 25,099 reports (88.1%) were PE-negative and 3,397 reports (11.9%) were PE-positive. The initial cohort selected included all patients for whom an annotated CTPA report was prepared in that timeframe. Temporally-linked ECG and EHR data were obtained for the patients in the cohort. After preprocessing and linking with the ECG datasets, a total of 23,793 CTPAs (10.0% positive for PE) and 320,746 ECGs (12.8% positive for PE) across 21,183 unique patients were available for model development and testing. Specifically, ECG data waveforms recorded at 500 Hz for 10 seconds (total of 5,000 data points) were available for all linearly independent leads: I, II, V1, V2, V3, V4, V5, and V6. FIG. 7 illustrates exemplary ECG data that was obtained for the study. The top of FIG. 7 includes examples ECG data with high voltage in precordial leads 705 that is physiologically appropriate while the bottom of FIG. 7 shows lower-quality ECG data 710. While both the top and bottom ECGs have high per-lead variance, the variance of the variance between leads is much larger for the bottom panel ECG than the top panel. The latter data was flagged for removal by a preprocessing algorithm.

In other implementations, different configurations of ECG data can be used. For example, ECG data can include single ECG data of variable time period, data of variable data frequency, and of variable numbers of leads that may or may not be independent. Additionally, the ECG data can include multiple ECGs, obtained at real time or in the past without limitation in their number and with continued update of the likelihood of PE Regarding the EHR data, database codes representing unique comorbidities, vital signs, and important labs were manually consolidated across the five hospital sites. ECG metadata was used to fill in missing demographics (age, sex, race) for patient encounters missing such data. Patients were only coded as having a comorbidity if the corresponding diagnostic codes were created before the start of the CTPA-related encounter. Vital signs including heart rate, blood pressure, respiration rate, temperature, oxygen saturation and laboratory results including D-Dimer, Brain-natriuretic peptide (BNP), and troponin-I were also extracted.

The CTPA data was filtered after initial collection to improve data quality. Natural Language Processing (NLP) of semi-structured reports was employed to determine PE status and to exclude scans ordered for an indication other than assessment of the pulmonary vasculature. All reports negative for a PE were identified by matching those containing a highly specific pattern. In the remaining reports, a team of medical practitioners annotated the scans for the presence, chronicity, and vascular location of a PE. Chronic PEs without any acute or subacute changes that may be associated with the presentation were classified as PE-negative to restrict the PE-positive class to only acute PEs causing the current symptomology. Given controversy over their clinical significance, CTPAs that only documented subsegmental PEs were also excluded. However, it is noted that this data can be treated differently. For example, the chronic PEs can be treated as PE-positive or segmental PEs can be included for training in various training implementations.

Figure 2:
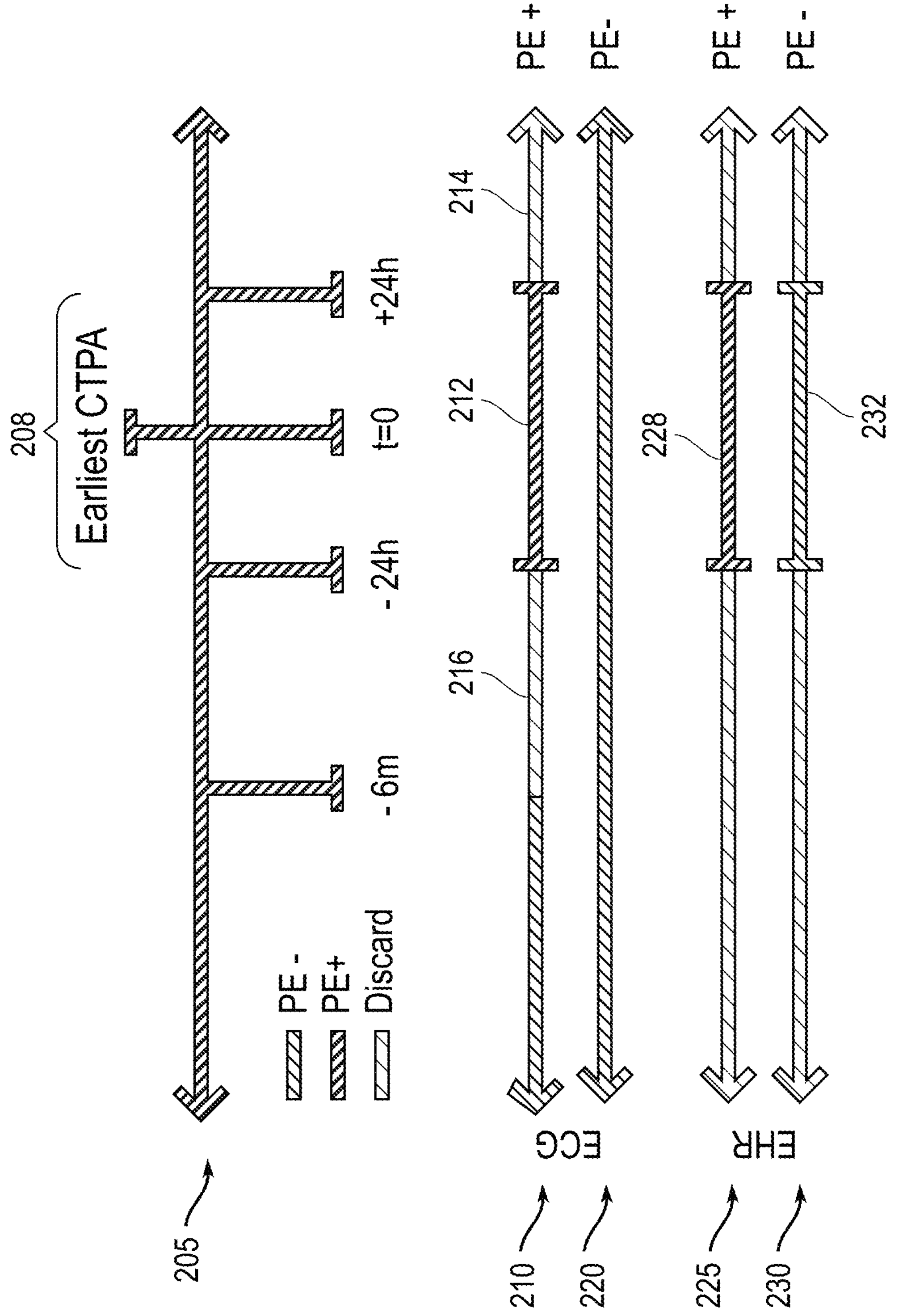
FIG. 2 is a schematic diagram showing the collection of CTPA, ECG and EHR data along a timeline according to an exemplary implementation of a PE prediction model as disclosed herein.

For a given patient encounter, ECGs and CTPAs were linked differently with one another depending on whether the CTPA was PE-positive or PE-negative. FIG. 2 is a schematic diagram showing the collection of CTPA, ECG and EHR data along a timeline according to the study. A first timeline 205 represents CTPA data collection. A region 208 of timeline 205 indicates a 48-hour window centered around the time at which the relevant CTPA scan was taken. ECG data is shown split into a PE-positive timeline 210 and a PE-negative timeline 220. Similarly, EHR data is shown split into a PE-positive timeline 225 and a PE-negative timeline 230. Referring to ECG timeline 210, labeled region 212 corresponds to the 48-hour window 208. ECGs recorded within this region 212 of the timeline were retained and labeled as PE-positive. ECGs taken after 24 hours of the CTPA shown in region 214, was discarded to minimize the impact of any medical intervention that may have started after the positive scan. Additionally, ECGs taken before 24 hours but less than six months of a positive CTPA, shown in region 216, were discarded since knowledge of when the PE began could not be assessed through ordinary means. With respect to the EHR data, respective regions 228, 232 of the PE-positive and PE-negative timelines that correspond to the 48-window were retained and labeled. All other EHR data was discarded.

Figure 3:
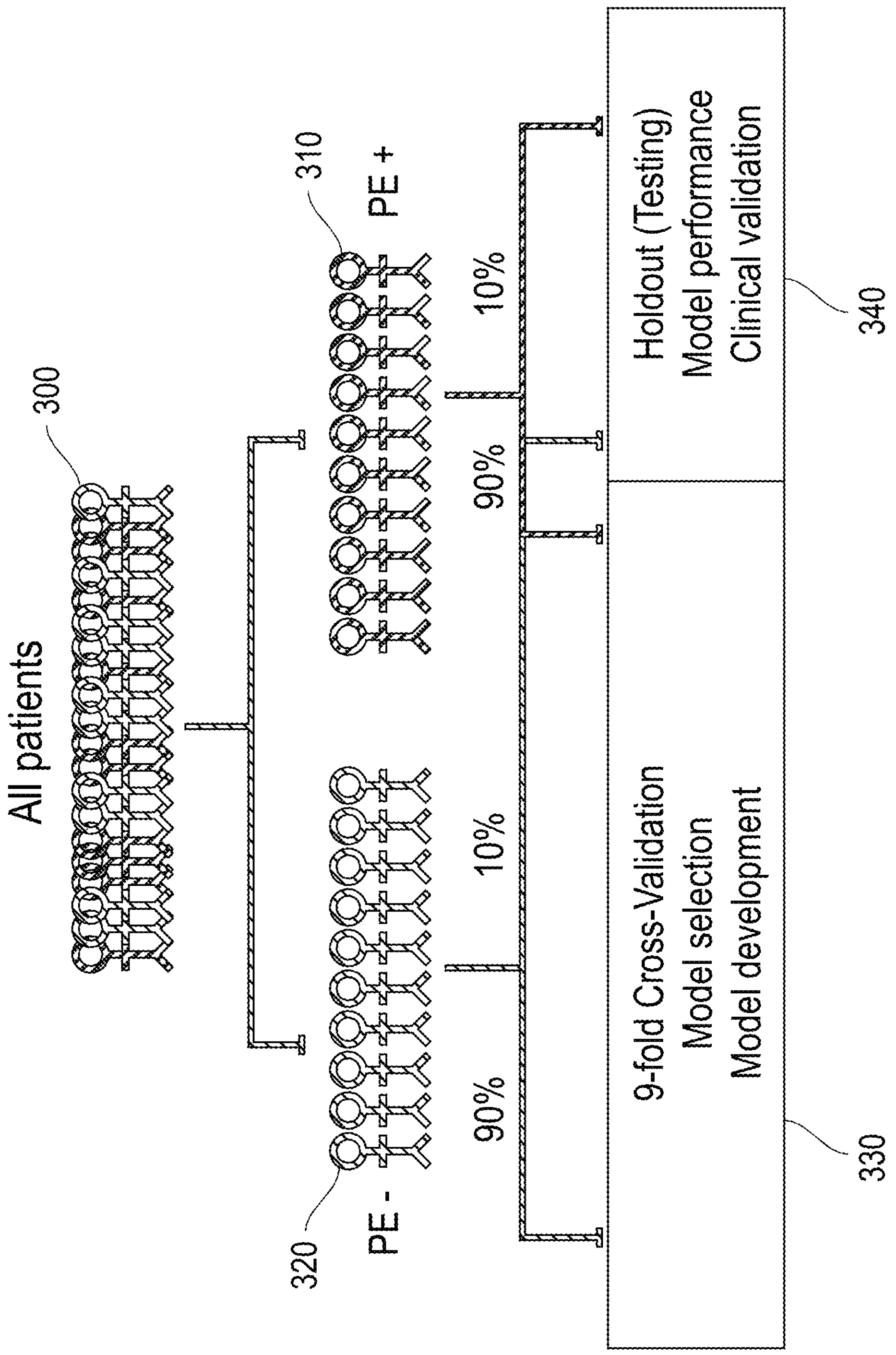
FIG. 3 is a schematic diagram that illustrates the division of the subsets of the population used for cross-validation and testing in the exemplary implementation of the PE prediction model.

The data yielded in this study affected model development. Given the low number of PE-positive CTPAs and the resulting class imbalance, a stratified k-fold approach was used to create the training, validation, and testing sets for the model. FIG. 3 is a schematic diagram that illustrates the division of the subsets of the population used for cross-validation and testing. In the study, the original patient data 300 was divided into those having at least one positive CTPA ("positive") 310 and those who have only negative CTPAs ("negative") 320 to ensure no leakage of patient data between the training, validation, and testing sets. However, this is not meant to be limiting and the deep learning framework for PE detection can designed without concern for data leakage between the training, validation, and testing sets. In the example model development, the subsets were split as follows: 90% for cross-validation (training and validation) and 10% for testing. Per the k-fold method, the cross-validation set was divided into nine folds to maintain an overall 80-10-10 training-validation-test split. The positive and negative patients from each split were combined to yield the final 9-fold cross-validation set 330 and holdout testing set 340. Given the prognostic severity of PEs, thresholds for classification were set at the greatest value (to maximize specificity) at which the models achieved 100% sensitivity (i.e. no false negative PEs) on the validation set. It is noted that there are other ways of prioritizing parameters for training and for displaying results to the clinician. In addition to maximizing specificity, the training thresholds can be set to prioritize accuracy, positive predictive value, negative predictive value, the area under the receiver operation characteristic curve (AUROC) and the area under the prediction-recall curve (AUPRC), or any combination thereof. Such prioritizations can be selectively performed on one or more subsets in the training set (e.g., based on severity of PE) and can be combined in a weighted fashion.

The output to the clinician can take many forms. The output can be binary, e.g., a yes/no result indicating whether or not PE is suspected. The output can also be formed in terms of a categorical likelihood as to whether PE is suspected (e.g., low, moderate, high). Alternatively, the output can be displayed as a continuous probability of suspected PE. Any of these can also be categorized further in terms of different subtypes of PE.

Figure 4:
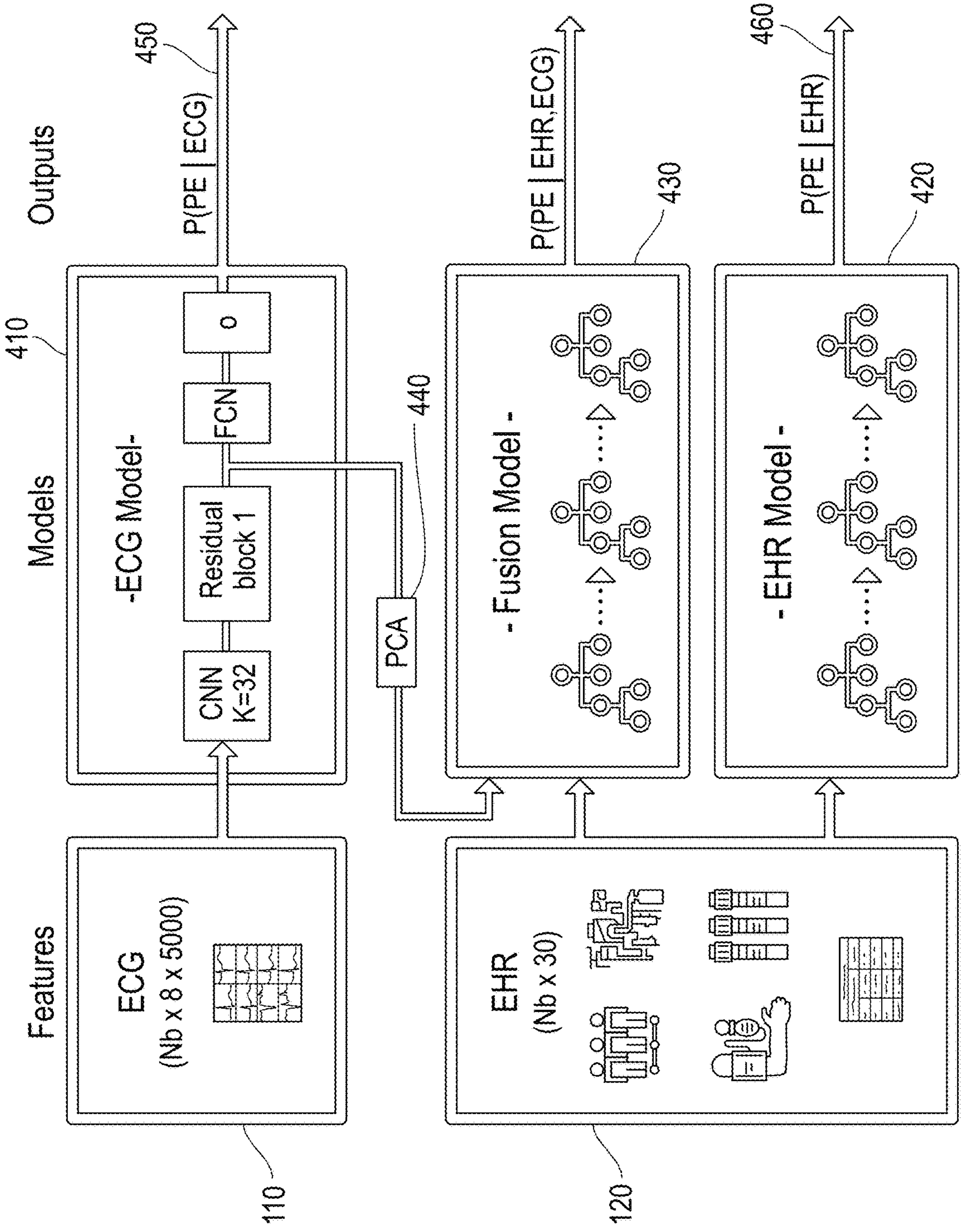
FIG. 4 is a schematic diagram that illustrates an example of model development in which two-different machine learning algorithms were compared to test the efficacy of using the input data categories alone versus combined in a multi-modal framework.

FIG. 4 is a schematic diagram that illustrates an example of model development in which three-different machine learning algorithms were compared to test the efficacy of using the input data categories alone versus combined in a multi-modal framework. A first machine learning algorithm 410 was trained on solely ECG data 110, a second machine learning algorithm 420 was trained on solely EHR data 420, and a third machine learning algorithm 430 combined EHR data and pre-processed and dimensionally-reduced data 440.

In the specific embodiment shown in FIG. 4, the ECG-only machine learning algorithm 410 applied a conventional neural network (CNN) model to ECG waveform data. The CNN network model ("ECG") was composed of a series of 12 residual blocks followed by a fully-connected layer and an output sigmoid activation layer. Each residual block in the CNN network was composed of two series of 1D-convolutional layers (the first with stride of 1, and the second with a stride of 2), a batch normalization layer, and a leaky ReLU activation layer with a residual connection. Either the block input for every other block, or the block input or the block input as passed through a second 1D-convolutional layer of stride 2 (every other block) were added to the output of the second batch normalization layer. These residual blocks created nested function classes in the neural network that promoted more expressive learning in successive layers rather than substantially different learning and lead to improved performance across multiple problem domains. In the specific embodiment, the convolutional layers had a kernel size of 15, padding of 7 (in each direction), and stride of 1 or 2 as appropriate. The number of channels for the convolutional layers were block dependent, starting at 32 and doubling every fourth block. Additionally, batch normalization was incorporated as a form of regularization and smoothing during training. Model weights were initialized using the Xavier initialization with a gain of 1. Models were trained with an Adam optimizer with an initial learning rate of 1e-3 for 30 epochs with a minibatch size of 128. A learning rate scheduler with decay on plateau was used to reduce the learning rate by a factor of 0.1 up to a minimum of 1e-7 in cases in which the difference in loss between successive epochs was less than 1e-3. A standard binary cross-entropy (BCE) loss was used to measure the error between predictions and labels. All implementations were carried out in PyTorch 1.5.1 with multi-GPU training across 4 NVIDIA V100 GPUS. The ECG model 410 yields a classification output 415, in this case a binary PE negative or positive classification.

For the EHR-only model 420, four classes of models were evaluated including logistic regression, ElasticNet, random forest, and Extreme Gradient Boosting (XGBoost) under different conditions. The EHR-only model 420 yielded a binary (PE positive/negative) classification as well.

The fusion modelling approach 430 combined ECG waveform data 110 and tabular EHR data 120. In contrast to the sole-ECG model 410, the ECG data 110 that was input to the fusion model 430 was first reduced in dimensionality since the fusion modeling dataset size was smaller (i.e., it included samples of patient-encounters versus samples of ECGs). In the depicted embodiment, principal components analysis (PCA) was used to reduce the dimensionality of this intermediate output to 20 components which is represented in FIG. 4 by PCA block 440. This lower-dimensional representation of ECG waveforms after PCA 440 was then combined with EHR data 120 and used as the input to each fusion model 430 tested. The use of independent PCA components proved beneficial for interpretability analysis. In the depicted embodiment, the fusion 430 model outputted a similar binary classification 435. ECGs for PE-negative patients recorded outside of the 24-hour window were not discarded, since these prior ECGs may still contain relevant information about a patient's clinical status. To predict PE from the fusion dataset, the best-performing model from the EHR experiments was selected as a scaffold to assess model robustness through feature sensitivity studies against a holdout test set.

Figure 5A:
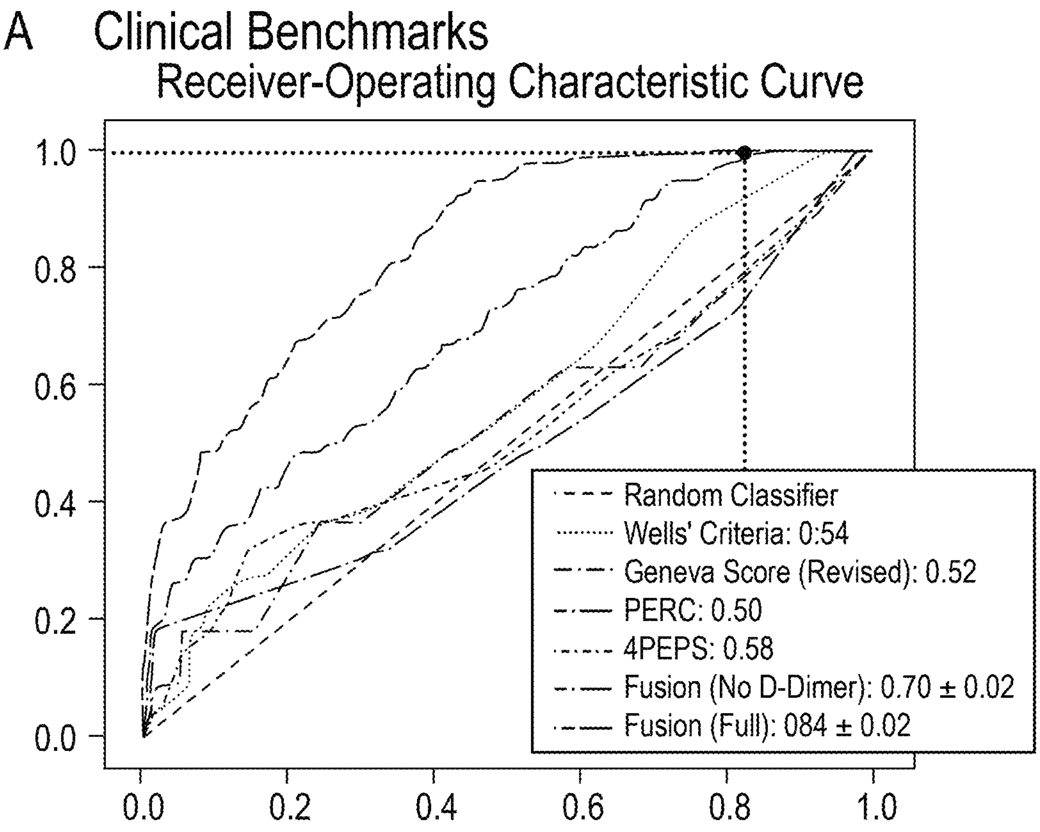
FIG. 5A shows receiver operating characteristic (ROC) curves of results of the testing of embodiments of the ECG, EHR and fusion models shown in FIG. 4.
Figure 5B:
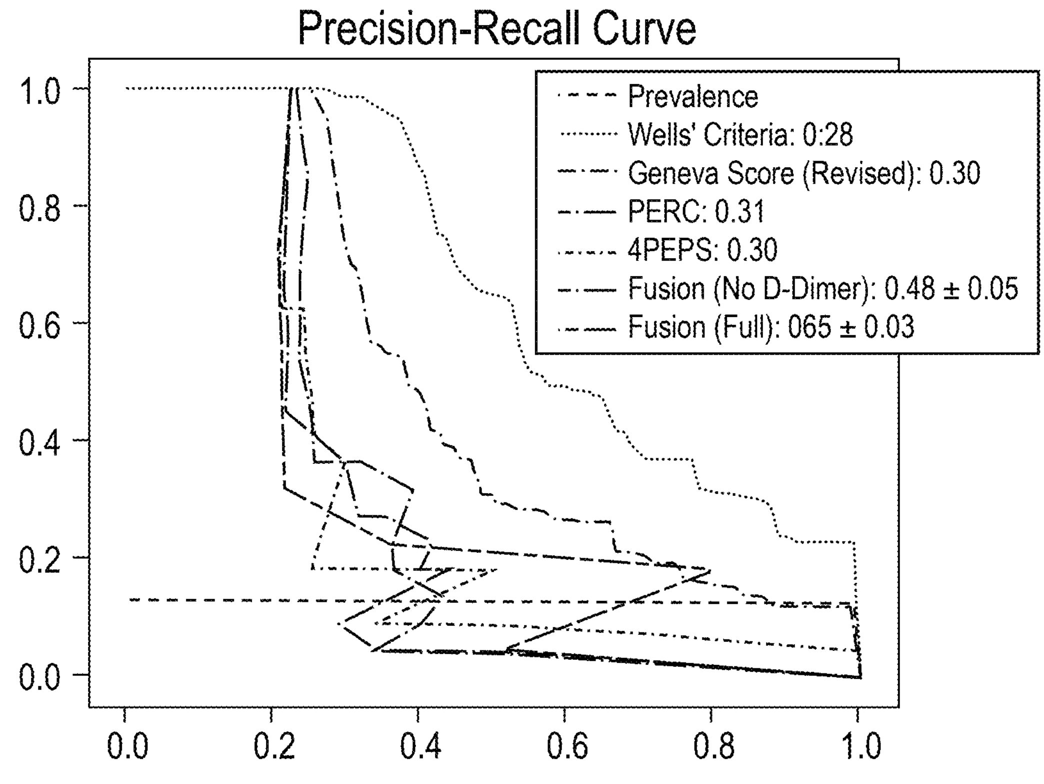
FIG. 5B shows precision-recall (PR) curves of results of testing of the embodiments of the ECG, EHR and fusion models shown in FIG. 4.

Performance of the models is shown in FIGS. 5A and 5B. FIG. 5A shows receiver-operating characteristic curves of the three models 410, 420, 430. The receiver-operating (ROC) curves plot the true positive rate (TPR) against the false positive rate (FPR) at different classification thresholds. Lowering the classification threshold classifies more items as positive, thus increasing both false positives and true positives. FIG. 5B shows precision-recall curves of the models 410, 420, 430. The precision recall (PR) curves plot the parameter true positives/(true positives plus false negatives) against the parameter true positives/(true positives plus false positives).

Figure 6:
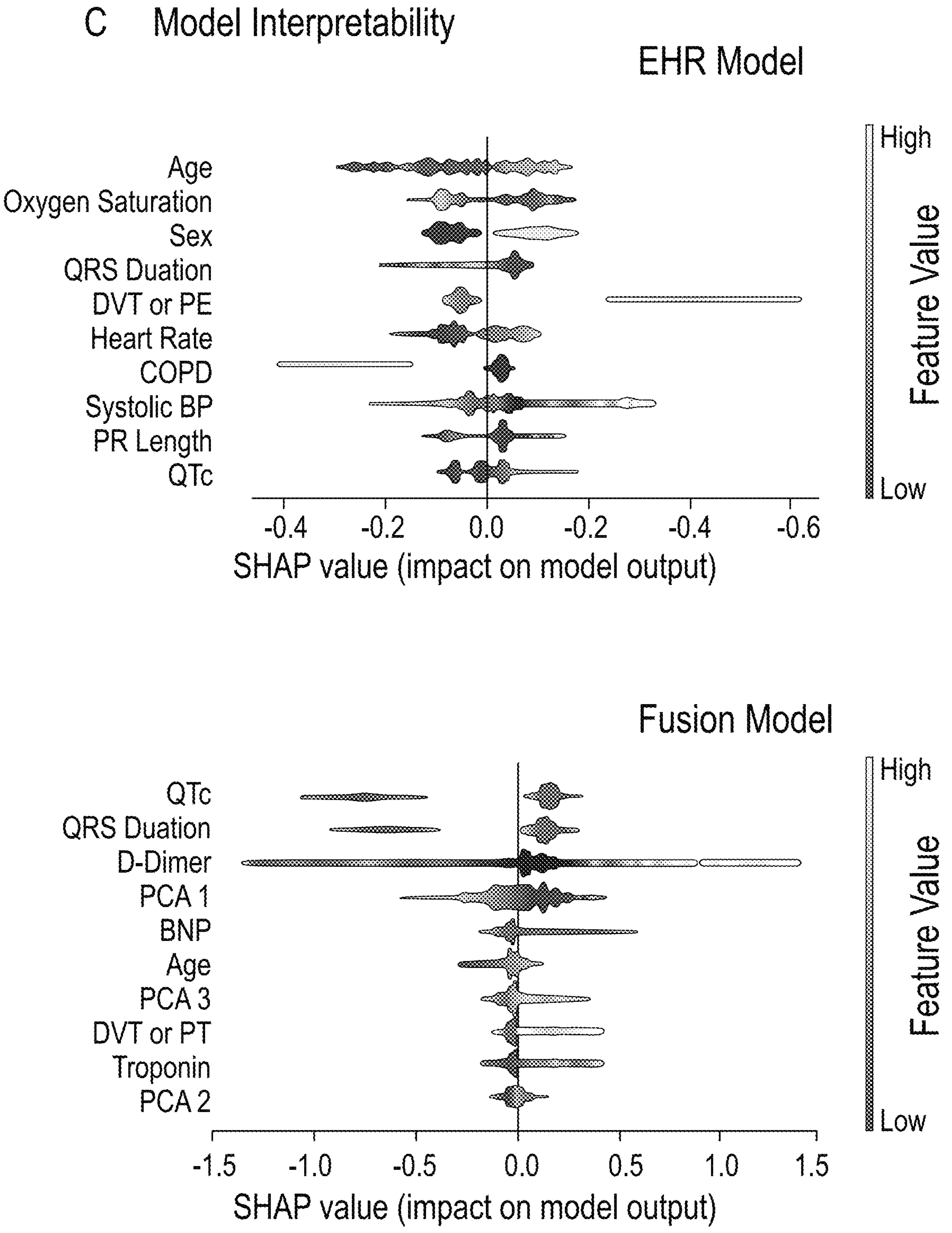
FIG. 6 shows Shapley Additive Explanations (SHAP) dependency plots of values against features for the embodiments of the EHR data and fusion models illustrated in FIG. 4.

Feature contributions toward model prediction were evaluated using Shapley Additive Explanations (SHAP) scores for the EHR model 420 and the fusion model 430. SHAP scores are a game-theoretic approach to model interpretability that provide explanations of global model structures based upon combinations of several local explanations for each prediction. To interpret and rank the significance of input features toward the final prediction of the model, mean absolute SHAP values were calculated for each feature across all observations in the holdout test set for each model trained on a cross-validation fold. FIG. 6 shows the SHAP dependency plots 610, 620 of the EHR model 420 and fusion model 430, respectively. In these plots the features are listed on the y-axis and the SHAP values measuring their impact on the model is plotted on the x-axis. In the model tests under discussion feature sensitivity analyses were also performed to investigate the effect of features that may cache clinician driven bias by assessing changes in model performance and their remove from the model input feature set (e.g., a BNP lab may be drawn if competing diagnoses, like CHF, are high in suspicion or may be a sign of PE prognostication).

After initial model training, the fusion model provided the best results, achieving an AUROC (the area under the receiver operating curve) of 0.82 on the cross-validation set, compared to AUROC results below 0.7 for both predicting PE based on the ECG-only or EHR-only data. On the holdout test set, the fusion model performed the best (AUROC of 0.81±0.01, AUPRC of 0.35±0.01), followed by the EHR model (AUROC 0.65±0.01, AUPRC 0.17±0.01) and the ECG model (AUROC 0.59±0.01, AUPRC 0.18±0.02). With respect to the ECG model, the performance using PCA components matched closely to the original CNN results. EHR model SHAP scores on this holdout set, shown in FIG. 6, demonstrated that higher values of age, male gender, history of deep vein thrombosis (DVT) or PE, absence of chronic obstructive pulmonary disease (COPD), higher heart rates, lower oxygen saturation, and lower QRS duration on ECG shifted the model output to predict PE, with the largest impact stemming from a positive history of DVT or PE (towards predicting PE) and positive history of COPD (towards predicting a absence of PE). Fusion model SHAP scores on the holdout set showed model output being driven more by continuous features, such that model output was shifted to predict PE with older age, higher D-dimer, higher QTc, lower QRS duration, lower values of the first principal component from the ECG waveform representation, and higher values of the third principal component. In subgroup analysis of model performance by PE location, all models detected truncal PEs the best, followed in order by main, lobar, and segmental PEs. There was comparable performance in the fusion model by gender (mean AUROC 0.81) and race (mean AUROC 0.77-0.84).

In addition, feature sensitivity experiments were performed. Model performance decreased with removal of D-Dimer data (AUROC 0.78±0.01), all labs (AUROC 0.76±0.01), and ECG morphology parameters (AUROC 0.75±0.01). The fusion model was overall well-calibrated (Brier score 0.076) and particularly had greater accuracy for negative-PE cases.

To understand the performance of these models relative to existing clinical screening tools for patients with CTPA (who are at moderate- to high suspicion of PE), the performance of the model was tested against common clinical criteria for assessing patient likelihood of having PE: Wells' Criteria for PE (Wells'), the Revised Geneva Score for PE (Geneva), PE Rule-Out Criteria (PERC)[29], and 4-Level PE Clinical Probability Score (4PEPS). To assess model performance, mean receiver operating characteristic (ROC) and mean precision-recall (PRC) curves with 95% confidence intervals (alpha=0.05) on the holdout test set across each fold were plotted and the mean and standard deviation areas under the ROC curve (AUROC) and PRC curve (AUPRC) were calculated. Statistical techniques such analysis of variance (ANOVA) was used to compare inter-model performance. Sensitivity, specificity, positive predictive value, and negative predictive value were estimated using the optimal threshold ensuring maximal sensitivity while maximizing specificity on the validation set.

Returning again to FIGS. 5A and 5B, the model performance was benchmarked against standard-of-care scoring systems through a threshold-independent metric (AUROC) and a threshold-dependent metric (specificity). On threshold-independent evaluation shown in FIGS. 5A and 5A, the fusion model with D-dimer (AUROC 0.84±0.02) and without D-dimer (AUROC 0.70±0.02) outperformed the clinical scores: Wells' criteria (AUROC 0.54), revised Geneva score (AUROC 0.52), PERC (AUROC 0.50), and 4PEPS (AUROC 0.58). When thresholding these scores based on published standards to exclude PE without the need for a D-dimer, the Wells' criteria score missed the most PEs (8), followed by the Geneva Score (7), and 4PEPS (3). Even when setting classification thresholds to achieve perfect sensitivity by adjusting the threshold for PE using the holdout test set, the fusion model without D-dimer had greater specificity (0.30) compared to 4PEPS (0.05), PERC (0.03), Wells' criteria (0.00), and the revised Geneva score (0.00) Another feature sensitivity study showed that the fusion model suffered minimally with removal of EHR data including demographics (AUROC 0.83), comorbidities (AUROC 0.83), vitals (AUROC 0.83), and ECG morphology parameters (AUROC 0.81).

The results demonstrate the efficacy of a model for detecting PE through a fusion modeling framework built on a large dataset of available clinical data and routinely collected ECG waveforms linked to annotated CTPA reports. The raw ECG waveform embeddings act synergistically with tabular discrete patient data to detect PE with greater specificity (AUROC 0.84, specificity 0.18) in those at moderate-to-high suspicion relative to commonly employed clinical scores (AUROC 0.50-0.58, specificity 0.00-0.05) in the test cohort. As noted above, despite the steady decrease in mortality attributable to PE, improving diagnostic yield remains important given that the condition remains underdiagnosed globally. However, given the high morbidity and mortality risk of PE, current clinical prediction models overpredict further workup with CTPA to reduce missed PEs. This causes an overreliance on CTPAs which results in greater patient exposure to contrast and ionizing radiation, contributes to increased patient time in the hospital, and worsens systemic inefficiencies. Furthermore, this CTPA utilization is more selectively increasing in older populations, who are at increased cancer risk from ionizing radiation.

Figure 8:
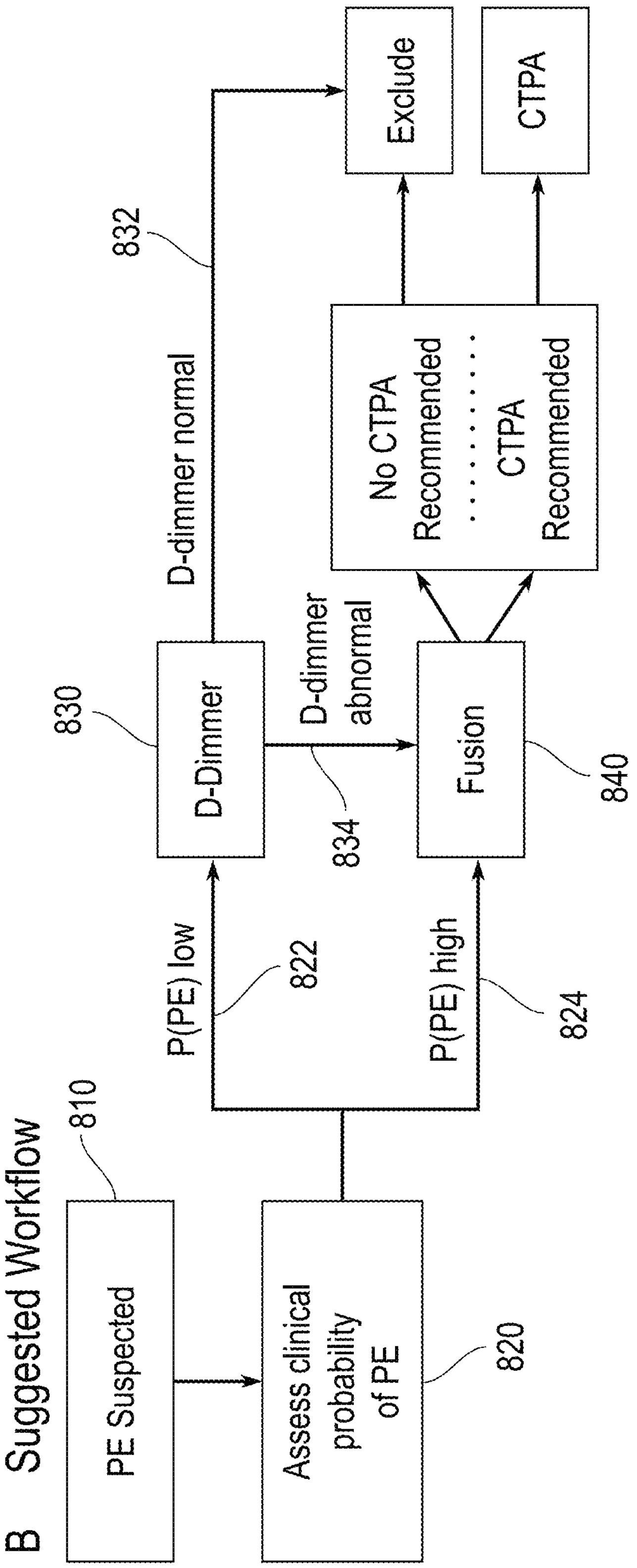
FIG. 8 is a block diagram of an exemplary implementation of a workflow for diagnosing PE in a clinical setting that employs the deep learning framework disclosed herein to prevent excess, non-indicated CTPA tests

FIG. 8 is a block diagram of an exemplary implementation of a workflow for diagnosing PE in a clinical setting that employs the deep learning framework disclosed herein to prevent excess, non-indicated CTPA tests. In a first step of the workflow 810, a patient suspected of having PE is introduced into a clinical setting. In step 820, a clinician performs an initial assessment of the likelihood of the patient having PE. The assessment in this implementation yields in either a low probability of PE (branch 822) or high probability of PE (branch 824). In other implementations, more detailed assessments of PE severity, location, etc. can be performed. After a low PE probability assessment (branch 822), a d-dimer test 830 is performed to confirm the assessment. If the d-dimer test is normal (branch 832), this confirms the low PE probability assessment, and the PE diagnosis is excluded. However, if the d-dimer result is abnormal (branch 834), this is a contraindication, and the low PE probability assessment is considered to be unconfirmed. However, even at this point, a CTPA is not ordered yet as would occur in current clinical settings. Rather, the patient's ECG and EHR (discrete) data is input to the fusion model in step 840. The model can output a binary result: either a negative recommendation 842 that no CTPA is need for the patient (based on a classification of the patient as having a low likelihood of PE) or a positive recommendation 844 to order a CTPA for the patient (based on a classification of the patient has having a high likelihood of PE). Here, the fusion model is an added gatekeeper preventing excessive performance of CTPA tests. It is noted that there are other actions that can be performed when the fusion model indicates a high likelihood of PE including, but not limited, to modification of pretest assessments of PE probability, ordering of additional laboratory tests and beginning empiric treatment with anticoagulation.

The deep learning framework disclosed herein can be implemented program instructions executable on a computer system and can be embodied on a computer-readable medium. Preferably, the program instructions are stored and executed on one or more processors operating in a cloud computing environment that can provide data collection, preprocessing, model development and execution and related capabilities to a client, such as a medical practitioner using a local computing device at a clinical facility, on an on-demand basis. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

In various embodiments, the cloud computing capabilities can be provided on one of a software-as-a-service (SaaS), platform-as-a-service PaaS) or infrastructure-as-a-service basis. SaaS enables clients to access cloud resources, e.g., via a web browser, and to use the provider's applications running on a cloud infrastructure. In PaaS, the client can deploy applications onto the cloud infrastructure using programming (e.g., APIs) supported by the cloud provider. PaaS gives the client some added control over the deployed applications and the hosting environment. With IaaS the client is accorded some control over the resources of the cloud infrastructure, including processing, storage, networks, and other fundamental computing resources.

Figure 9:
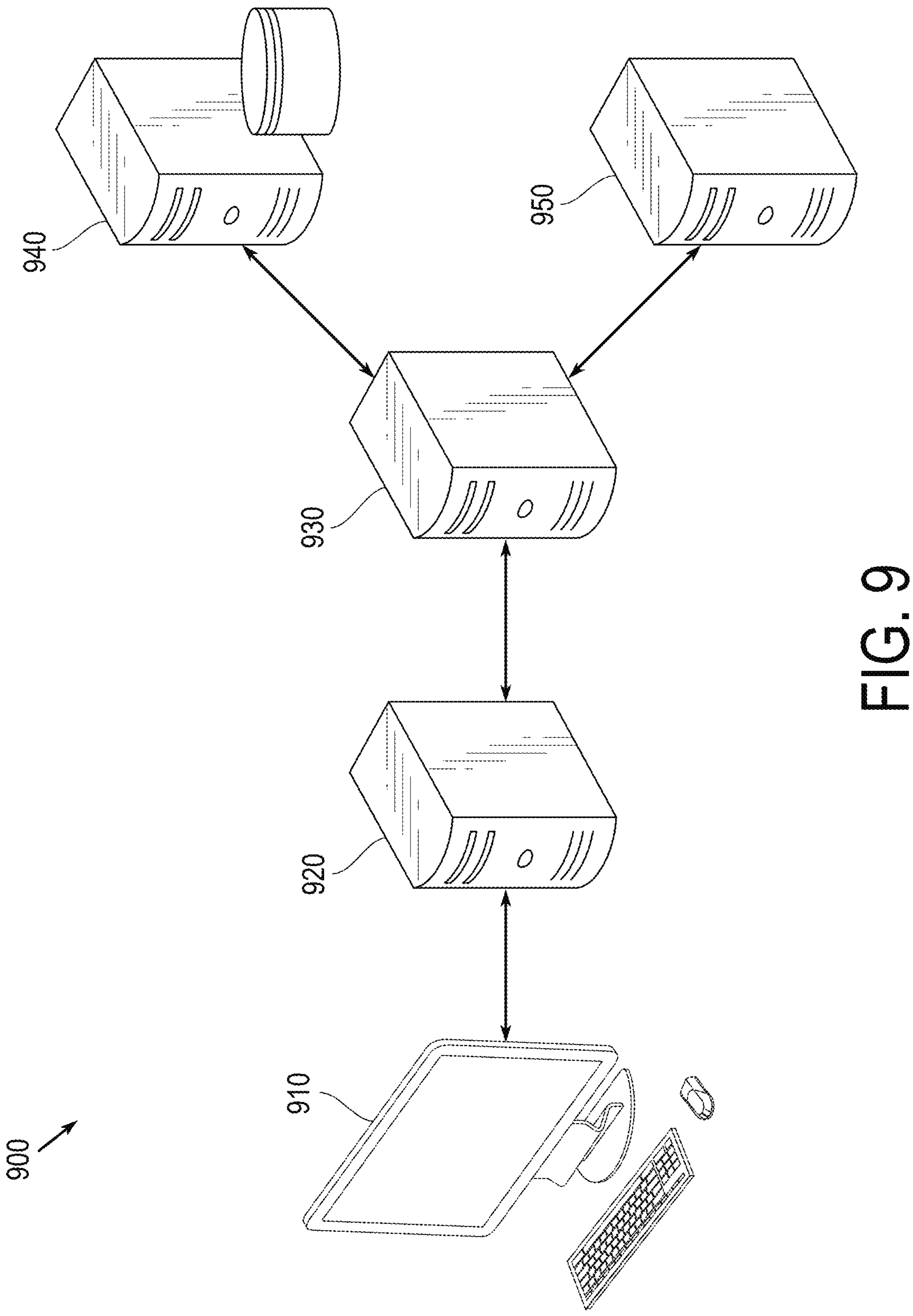
FIG. 9 is a schematic diagram showing a portion of a relevant portion of an exemplary cloud computing environment for training and executing a deep learning model for PE detection according to the present disclosure.

FIG. 9 is a schematic diagram showing a portion of a relevant portion of an exemplary cloud computing environment 900 for training and executing a deep learning model as described herein. All of the component of the cloud computing environment are communicatively coupled via a cloud network. At an edge of the cloud computing environment 900 is a client computer 910 ("client"). The client 910 can be any computing device having suitable computing resources as known in the art (e.g., desktop or laptop computer, tablet, mobile device). As one example, the client can be a computer device at a clinical facility from which a medical practitioner or other specialist may access the cloud computer environment 900. The client 910 is communicatively coupled to a private or public network through which a cloud server 920 can be accessed. In some implementations, the client 910 executes a web browser application through which a user can interact via a user interface and the cloud server 920 is a web server that interacts with the client web browser application. Cloud server 920 is, in turn, communicatively coupled to an application server 930 via, for example, an application program interface (API). The application server 930 can be configured to run a machine learning platform. In association with the API, the application server 930 preferably provides an interface through which a user at client 910 can interact with the machine learning platform. The machine learning platform can enable the user to upload data, implement program code for a machine learning model, configure various parameters (e.g., hyperparameters) of a model, and execute model training, testing and execution. The application server 930 can obtain data directly from the client, but this may not be the most efficient way to provision the machine learning platform with data. For this purpose, the application server 930 can obtain information directly from database servers 940, 950 over the cloud network. In one example, database server 940 stores and provides EHR data and database server 950 stores and provides ECG and CTPA image data. This is merely an illustrative example and all types of data can be stored and provided by a single database server, or numerous different servers can store and provide different permutations of HER, ECG and CTPA data. Similarly, it is noted that the application server 930 can be implemented as a standalone server or can operate in conjunction with other network nodes in the cloud computing environments whereby tasks are distributed and performed by linked processing devices in the cloud network. In the cloud computing environment, program modules may be located in both local and remote computer system storage media including memory storage devices.

Figure 10:
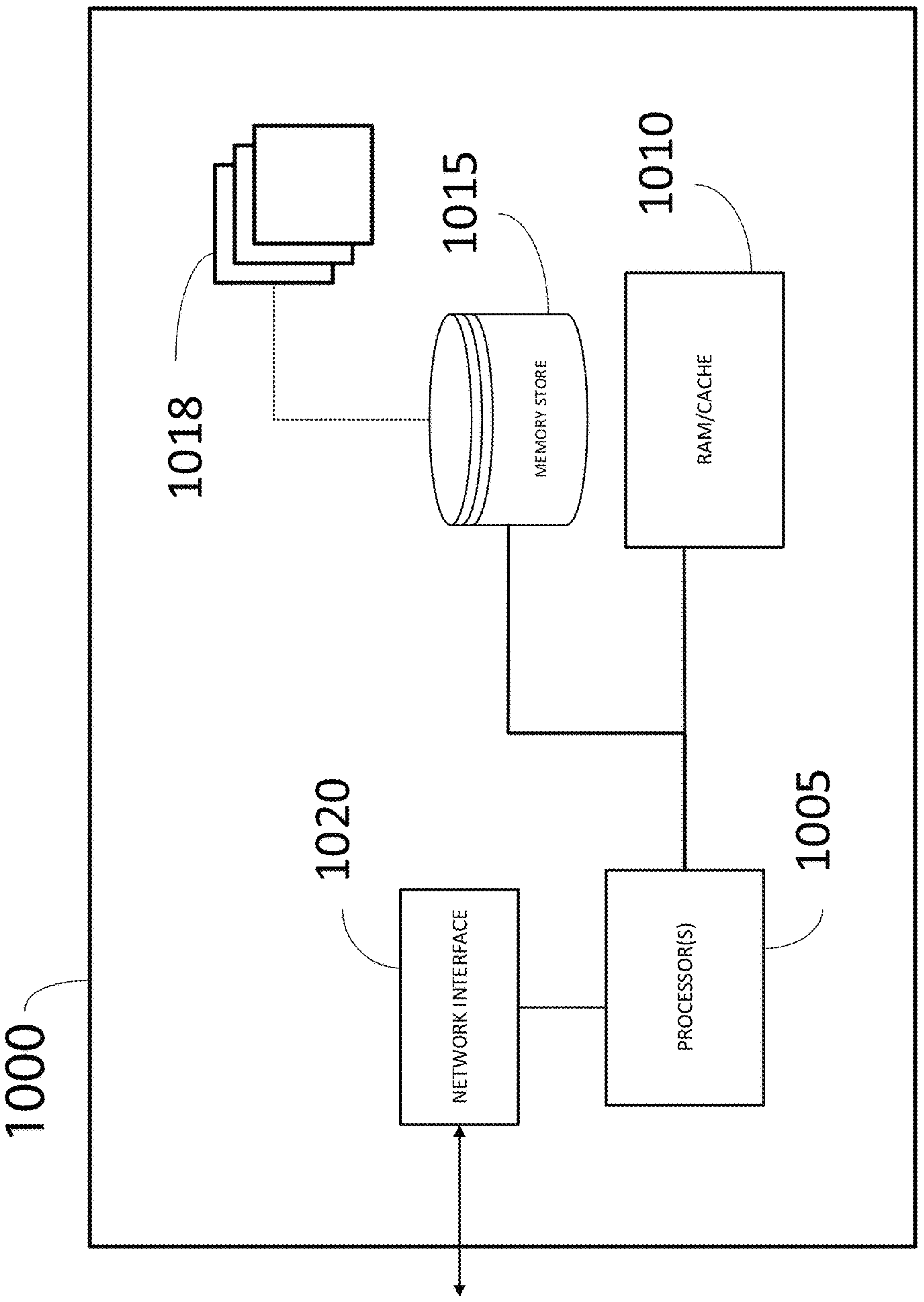
FIG. 10 a schematic block diagram of an exemplary application server that can be configured to run a machine learning platform for executing a deep learning model for PE detection according to the present disclosure.

FIG. 10 is a schematic block diagram depicting an exemplary application server 930 that can be employed to execute methods disclosed herein. Application server includes one or more general-purpose or specific processing units 1005 (e.g., graphic processing units (GPUs). The processing unit(s) 1005 is coupled via a bus to local memory RAM/cache storage 1010 as well as system memory 1015. A network interface 1020 is used to communicatively link the application server to other nodes in the cloud network. System memory 1015 can comprise a variety of computer system readable media including both volatile and non-volatile media, removable and non-removable media such as a hard drive. The system memory 1015 stores a set of program modules 1018 that can be used to implement the functionality of the application server including providing a machine learning platform and executing the deep learning PE detection model disclosed herein.

It is to be understood that any structural and functional details disclosed herein are not to be interpreted as limiting the systems and methods, but rather are provided as a representative embodiment and/or arrangement for teaching one skilled in the art various ways to implement the methods. It is to be further understood that like parts in the drawings represent like elements through the several figures, and that not all components and/or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the disclosure as understood by a person having ordinary skill in the art.

What is claimed is:

1. A method of training a computer system to predict whether a patient has a pulmonary embolism (PE) based on discrete patient data and ECG waveform data, the method comprising:

gathering training data pertaining to a patient population, the training data comprising, for each member of the patient population, computer tomography pulmonary angiogram (CTPA) data, discrete patient data including patient related clinical and demographic data, and ECG waveform data, at least some of the CTPA data being annotated to indicate a PE classification or likelihood; and training a deep learning multimodal fusion model on the training data, the model to output predicted PE classifications or likelihoods from input comprising the ECG waveform data and the discrete patient data, the training determining weightings of various features of the input that optimize an accuracy of a match to the PE classifications or likelihoods of the annotated CTPA data.

2. The method of claim 1, wherein the deep learning multimodal fusion model is trained using a supervised deep learning technique.

3. The method of claim 1, wherein the deep learning multimodal fusion model is trained using a semi-supervised learning technique.

4. The method of claim 1, wherein the deep learning multimodal fusion model is trained using a self-supervised learning technique.

5. The method of claim 1, wherein the ECG waveform data is obtained directly from the patient.

6. The method of claim 1, further comprising, before training, generating synthetic ECG waveform data based on original patient ECG waveform data.

7. The method of claim 6, wherein the synthetic ECG waveform data is generated using an adversarial network.

8. The method of claim 1, wherein for each member of the population, the CTPA data is annotated in accordance with a binary PE classification as positive, indicating presence of PE, or negative, indicating absence of PE.

9. The method of claim 1, wherein for each member of the population, the CTPA data is annotated to indicate a severity, chronicity, or location of PE found.

10. The method of claim 1, further comprising:

prior to training the multimodal fusion model, processing the ECG waveform data using a machine learning technique and a dimensionality reduction technique.

11. The method of claim 10, wherein the dimensionality reduction technique is a linear technique including at least one of Factor Analysis (FA), Linear Discriminant Analysis (LD), and Truncated Singular Value Decomposition (SVD).

12. The method of claim 10, wherein the dimensionality reduction technique is a non-linear technique including at least one of Kernel PCA, t-distributed Stochastic Neighbor Embedding (t-SNE), Multidimensional Scaling (MDS), and Isometric mapping (Isomap).

13. The method of claim 10, wherein the dimensionality reduction technique is a feature elimination technique.

14. The method of claim 13, wherein the dimensionality reduction technique is a random forest technique.

15. The method of claim 10, wherein the ECG waveform data is preprocessed using a machine learning technique selected from the group consisting of: a convolutional neural network, a recurrent neural network, a long-term-short-term memory network, a graph neural network, and a transformer network.

16. The method of claim 1, wherein the discrete patient data includes at least a brain natriuretic peptide (BNP) level, D-dimer level, and a troponin level.

17. The method of claim 1, wherein the discrete patient data includes at least a brain natriuretic peptide (BNP) level, D-dimer level, troponin level, age, sex, and cardiac-related comorbidity information.

18. The method of claim 1, wherein the ECG waveform data and CTPA data were generated within a defined period from each other.

* * * * *